United States Patent
Ashby et al.

(10) Patent No.: US 8,980,593 B1
(45) Date of Patent: Mar. 17, 2015

(54) PRODUCTION OF TUNABLE POLYHYDROXYALKANOATE BIOPOLYMERS USING GLYCEROL AND LEVULINIC ACID

(71) Applicant: The United States of America, as represented by the Secretary of Agriculture, Washington, DC (US)

(72) Inventors: Richard D Ashby, Glenside, PA (US); Daniel K. Y. Solaiman, Dresher, PA (US); Gary D Strahan, Baltimore, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 202 days.

(21) Appl. No.: 13/678,945

(22) Filed: Nov. 16, 2012

Related U.S. Application Data (60) Provisional application No. 61/560,557, filed on Nov. 16, 2011.

(51) Int. Cl.
*C12P 7/62* (2006.01)
*C08G 63/06* (2006.01)

(52) U.S. Cl.
CPC .................................... *C12P 7/625* (2013.01)
USPC ........................................ 435/135; 528/361

(58) Field of Classification Search
CPC ..................................................... C12P 7/625
See application file for complete search history.

(56) References Cited

U.S. PATENT DOCUMENTS

| | | | |
|---|---|---|---|
| 6,225,438 B1 | 5/2001 | Green | |
| 6,649,380 B1 | 11/2003 | Yano et al. | |
| 2012/0135480 A1* | 5/2012 | Nakas et al. | 435/135 |

OTHER PUBLICATIONS

Zhu et al, American Institute of Chemical Engineers, Production and Characterization of Poly-3-hydroxybutyrate From Biodiesel-Glycerol by *Burkholderia cepacia* ATCC 17759, 2009, pp. 424-430.*
Ashby, R.D., et al., Glcerine and Levulinic Acid: Two Valuable Co-Products for the Fermentative Synthesis of Poly (hydroxyalkanoate) Biopolymers, 102nd AOCS Annual Meeting & Expo, May 1-4, 2011, Cincinatti, OH.
Ashby, R. et al., Efficient Utilization of Crude Glycerol as Fermentation Substrate in the Synthesis of Poly(3-hydroxybutyrate) Biopolymers, J. Am Oil Chem Soc, (2011) 88: 949-959.
Keenan, T., et al., Production and Characterization of Poly-Beta-hydroxyalkanoate Copolymers from *Burkholderia cepacia* Utilizing Xylose and Levulinic Acid, Biotechnol Prog. 2004, (20), 1697-1704.
Kulkarni, S.O., et al., Production and characterization of a biodegradable poly (hydroxybutyrate-c-hydroxyvalerate) (PHB-co-PHV) copolymer by moderately haloalkalitolerant Halomonas campisalis MCM B-1027 isolated from Lonar Lake, India, Bioresource Technology 101, 2010, 9765-9771.
Modi, S., et al., Therman and Rheological Properties of PHB Synthesized with Various Hydroxyvalerate Content Potential Use in Food Packaging, ANTEC, 2009, 1636-1640.
Vishnuvardhan Reddy, S., et al., Production of PHB and P (3HB-co-3HV) biopolymers by *Bacillus megaterium* strain OU303A isolated from municipal sewage sludge, World J Microbiol Biotechnol, 2009, 25: 391-397.
Yu, J. et al., Biopolyester Synthesis and Protein Regulations in *Ralstonia eutropha* on Levulinic Acid and Its Derivatives from Biomass Refining, J. of Biobased Materials and Bioenergy, 2009, vol. 3, 113-122.

* cited by examiner

*Primary Examiner* — Paul A Zucker
(74) *Attorney, Agent, or Firm* — Gail E. Poulos; David L. Marks; John D. Fado (57) ABSTRACT

This invention relates to the production of short-chain polyhydroxyalkanoate biopolymers which include C3 to C5 3-hydroxyacyl monomers. The process includes culturing a native microorganism capable of synthesizing polyhydroxyalkanoate biopolymers using as a carbon source an amount of glycerol, levulinic acid and mixtures thereof that drives the microbial synthesis of polyhydroxyalkanoate biopolymers.

5 Claims, 6 Drawing Sheets
(3 of 6 Drawing Sheet(s) Filed in Color)

¹H-NMR of the polymer samples derived from the 10-L fermentations containing glycerine:levulinic acid ratios of 1%:0 (A), 0.75%:0.25% (B), 0.5%:0.5% (C) and 0.25%:0.75% (D).

FIG. 4

PRODUCTION OF TUNABLE POLYHYDROXYALKANOATE BIOPOLYMERS USING GLYCEROL AND LEVULINIC ACID

RELATED APPLICATION

This application is claims priority to U.S. Provisional Patent Application Ser. No. 61/560,557, filed Nov. 16, 2011 the contents of which are incorporated herein by reference in their entirety.

BACKGROUND OF THE INVENTION

1. Field of the Invention

The present invention relates to biopolymer production and in particular to a novel process for microbiologically producing short-chain polyhydroxyalkanoate (PHA) biopolymers using glycerol (glycerine) and levulinic acid as fermentation feedstocks. Furthermore the present invention relates to the production of short-chain PHA biopolymers having tunable monomer compositions and material properties using varying ratios of glycerol and levulinic acid.

2. Description of the Related Art

Increased environmental concern has prompted the search for "green" substitutes for many petroleum-based materials including transportation fuels, chemicals, and polymers. This search has lead to the development of novel uses for renewable and sustainable feedstocks as precursors for these bio-based products. Unfortunately, experience has shown that synthesis of bio-based materials generally involves higher overhead costs than petroleum-based products thereby hindering extensive use of bio-based materials in industrial applications.

Biopolymers are one class of chemicals that are currently receiving increased consideration as possible substitutes for petroleum-based polymers. However, successful replacement can only be realized if the biopolymers can be produced in adequate quantities from low-cost feedstocks and exhibit properties that are at least equivalent to their synthetic counterparts. Glycerol is one feedstock that is being assessed for new applications in both chemical and biological syntheses. It is created as a co-product in the base-catalyzed transesterification of triacylglycerols (TAGs) with short-chain alcohols, generally methanol in the biodiesel production process.

Historically, glycerol has been used in the drug, food, beverage, chemical and synthetic material industries. However, these applications normally require a high quality glycerol. The transesterification reaction involved in the biodiesel production process results in a crude glycerol component whose composition differs based on the type of TAG used, the efficiency of the transesterification reaction and the effectiveness of biodiesel and alcohol recovery. Yet, because of the rapid expansion of the biodiesel industry, glycerol is being produced at levels that have caused its value to drop to historic lows. While the price has recovered somewhat, the expected pace of future biodiesel production necessitates new uses for glycerol to help maintain some value.

Poly(hydroxyalkanoates) (PHA) represent a family of biodegradable bacterial polyesters that are synthesized as carbon and energy reserves by numerous bacterial species from many different carbon substrates (Huijberts, G. N. M., et al., Appl. Environ. Microbiol., 58: 536-544 (1992); Eggink, G., et al., Ind. Crops Products, 1: 157-163 (1993); de Smet, M-J., et al., J. Bacteriol., 154: 870-878 (1983); Ashby, R. D., and T. A. Foglia, Appl. Microbiol. Biotechnol., 49: 431-437 (1998); Solaiman, D. K. Y., et al., Curr. Microbiol., 44: 189-195 (2002). Synthesis generally occurs when a surplus of exogenous carbon is present and cellular growth is impeded by the lack of some other essential nutrient. PHA biopolymers are generally classified into 3 groups based on the length of their side-chains. Short-chain-length PHA (scl-PHA) polymers consist of 3-hydroxyalkanoic acids with monomeric repeat units of 3-5 carbons, medium-chain-length PHA (mcl-PHA) polymers are composed of monomeric repeat units that are 6-12 carbons in length, and long-chain-length PHA (lcl-PHA) polymers are comprised of monomeric repeat units ≥13 carbons. Because of their side-chain length and structural variability, PHA polymers exhibit a wide array of material properties from rigid thermoplastics to amorphous elastomers. Poly(3-hydroxybutyrate) (PHB), the simplest of the PHA biopolymers, was first discovered in 1926 and has been the best-characterized polymer within the PHA family (Lemoigne, M., Bull. Soc. Chem. Biol. (Paris), 8: 770-782 (1926)). It has been favorably compared to the petroleum-based polypropylene (PP) and polyethylene (PE) with respect to its environmental impact and its material properties. Life cycle analysis (LCA) showed that PHB was better than PP and PE in environmental impact by surpassing both PP and PE in its effects on abiotic and ozone depletion, global warming, human and ecotoxicity, acidification and eutrophication (Harding, K. G., et al., J. Biotechnol., 130: 57-66 (2007)). However, because of its highly crystalline nature, PHB is considered too rigid and brittle for widespread industrial application. To improve the material properties of these polymers, studies shifted to the production of copolymers to reduce the crystallinity of the material and to make it more ductile while at the same time decreasing the melting temperature to simplify processing conditions. Monomers such as 4-hydroxybutyric acid (4-HB), 3-hydroxyvaleric acid (3-HV), 4-hydroxyvaleric acid (4-HV), 3-hydroxyhexanoic acid (3-HHx) and 3-hydroxyoctanoic acid (3-HO) among others have been successfully copolymerized with 3-hydroxybutyric acid (3-HB), and in each case the material properties were improved over the PHB homopolymer (Kunioka, M., et al., Appl. Microbiol. Biotechnol., 30: 569-573 (1989); Holmes, P. A., et al., U.S. Pat. No. 4,477,654; Valentin, H. E., Appl. Microbiol. Biotechnol., 36: 507-514 (1992); Doi, Y., et al., Macromolecules, 28: 4822-4828 (1995); Budde, C. F., et al., Appl. Environ. Microbiol., 77: 2847-2854 (2011); Lianggi, Z., et al., Lett. Appl. Microbiol., 42: 344-349 (2006)).

Poly(3-hydroxybutyrate-co-3-hydroxyvalerate) (PHB/V) is one of the PHA copolymers that has drawn interest. It is easy to synthesize and has been shown to possess a good balance of tensile strength and ductility and exhibits more desirable mechanical properties than PHB. Historically, PHB/V was synthesized using various combinations of simple sugars and either propionic acid or pentanoic (valeric) acid to vary the 3-HB:3-HV ratios within the copolymers (Pereira, S. M. F., et al., Polym. Engin. Sci., 48: 2051-2059 (2008); Yu, S. T., et al., Proc. Biochem., 40: 2729-2734 (2005)). Acetyl CoA has long been known to be the precursor molecule in the synthesis of PHB. It is synthesized through substrate level phosphorylation and can be utilized either as an energy and metabolite precursor in the tricarboxylic acid cycle (TCA) or can be used by the microorganism to produce PHA biopolymers. In *Ralstonia eutropha*, the most studied PHB producing bacterial strain, production begins through the condensation of one acetyl-CoA molecule with another to produce acetoacetyl-CoA by the action of the 3-ketothiolase enzyme. Acetoacetyl-CoA is then reduced to 3-hydroxybutyryl-CoA by acetoacetyl-CoA reductase and finally polymerized by the action of PHA synthase (Madison, L. L., and G. W. Huisman, Microbiol. Molecul. Biol. Rev., 63: 21-53 (1999)). When propionic acid is introduced as a co-substrate, propionyl-CoA is created which can condense with acetyl-CoA to produce the 5-carbon precursor, 3-ketovaleryl-CoA. This molecule is then further reduced to 3-hydroxyvaleryl-CoA and polymerized into the growing polymer chain (Doi, Y., et al., Macromolecules, 20: 2988-2991 (1987); Bramer, C. O., and A. Steinbuchel, Microbiology, 147: 2203-2214 (2001)). When grown in the presence of pentanoic (valeric) acid, the acid must first be enzymatically converted to valeryl-CoA, and then converted to 3-hydroxyvaleryl-CoA before it can be incorporated into the growing polymer backbone (Page, W. J., et al., Appl. Environ. Microbiol., 58: 2866-2873 (1992); Yu, J., et al., J. Biobased Mat. Bioenergy, 3: 113-122 (2009)). In both cases, under appropriate fermentation conditions, the use of propionic acid and/or pentanoic (valeric) acid as co-substrates with simple fermentable sugars results in PHB/V copolymers.

Since raw material costs account for the majority of the overall production cost of these biopolymers, efforts have been made to produce PHA polymers from less expensive starting materials. Some of these efforts have included such raw materials as soy molasses, wheat-based co-products, and glycerol (Solaiman, D. K. Y., et al., Biotechnol. Lett., 28: 157-162 (2006); Koutinas, A. A., et al., Enz. Microb. Technol., 40: 1035-104 (2007); Xu, Y., et al., Proc. Biochem., 45: 153-163 (2010); Ashby, R. D., et al., J. Polym. Environ., 12: 105-112 (2004); Cavalheiro, J. M. B. T., et al., Proc. Biochem., 44: 509-515 (2009); Shrivastav, A., et al., Int. J. Biol. Macromol., 47: 283-287 (2010); Zhu, C., et al., Biotechnol. Prog., 26: 424-430 (2010); Mothes, G., et al., Eng. Life Sci., 7: 475-479 (2007); Kawata, Y., et al., Biosci. Biotechnol. Biochem., 74: 175-177 (2010)). Under the conditions employed in each of these studies, PHB homopolymers were synthesized; however, in combination with other renewable inexpensive carbon sources, the possibility exists that co-polymeric PHA can be produced that exhibit improved material properties over PHB at reduced cost.

Glycerol is an inexpensive, renewable co-product that has drawn interest as a substrate for PHA polymer synthesis. Glycerol is derived from the base-catalyzed transesterification of triacylglycerols (TAGs) in the production of biodiesel. Due to the large amounts of biodiesel being produced worldwide, glycerol is flooding the market and driving its value down to a few cents per pound, making it more attractive as a feedstock for a number of value-added bio-based materials including 1,3-propanediol (Mu et al., Biotechnol. Lett., 28: 1755-1759, 2006), propylene glycol (Dasari et al., Appl. Catal. A: General 281, 225-231, 2005), epichlorohydrin (Santacesaria et al., Ind. Eng. Chem. Res., 49, 964-970, 2010), 3-hydroxypropionic acid (Raj et al., Proc. Biochem., 43, 1440-1446, 2008), succinic acid (Scholten et al., Biotechnol. Lett., 31: 1947-1951, 2009) citric acid (Papanikolaou and Aggelis, Lipid Technol., 21: 83-87, 2009), acrylic acid (Witsuthammakul and Sooknoi, Appl. Catal. A: General, 413-414, 109-116, 2012) single cell oils (Papanikolaou and Aggelis, supra), and glycolipid bio surfactants (sophorolipids) (Ashby et al 2005a), among others.

Levulinic acid synthesis is based on cellulosic waste materials. Because of this, economic projections indicate that levulinic acid production costs could fall to as low as $0.04-$0.10/lb depending on the scale of operation (Bozell et al., Res. Conserv. Recycl., 28, 227-239, 2000). Since levulinic acid is cheap and is a structural analogue of pentanoic acid, it has been assessed as a secondary substrate in PHA biosynthesis. Results have shown that elevated concentrations of levulinic acid tend to be toxic to many microorganisms, but success in the production of PHB/V biopolymers has been realized when low concentrations of levulinic acid were used in combination with other less harmful substrates. To this end, PHB/V copolymers have been produced from levulinic acid when used in conjunction with typical monosaccharide co-substrates such as glucose (Jang and Rogers, Biotechnol. Lett., 18, 219-224, 1996), fructose syrup (Chung et al., J. Microbiology, 39, 79-82, 2001), xylose (Keenan et al., Biotechnol. Prog., 20, 1697-1704, 2004) and gluconic acid (Kim et al., J. Microbiol., 47, 651-656, 2009) however; the maximum 3-HV content realized in these studies was 86 mol % regardless of the bacterial strain used. Other researchers successfully produced terpolyesters containing 3-HB, 3-HV and 4-HV from levulinic acid under controlled conditions (Gorenflo et al., Biomacromolecules, 2, 45-57, 2001, Yu et al., J. Biobased Mat. Bioenergy, 3, 113-122, 2009).

Thus there is a need to make PHA biopolymers more economical and impart additional value to glycerol. Glycerol and levulinic acid were used as low-cost fermentative co-substrates in the synthesis of PHB/V copolymers with wide-ranging 3-HB:3-HV ratios. While various methods for making biodegradable polyesters have been developed, there remains a need in the art for a method of making biocompatible and biodegradable polyesters with tunable properties from two large-volume, low-value coproducts. The present invention described below includes such methods which are different from related art methods for producing bacterial biodegradable polyesters.

SUMMARY OF THE INVENTION

It is therefore an object of the present invention to provide a fermentation method for producing short-chain polyhydroxyalkanoate (PHA) biopolymers having tunable monomer compositions wherein said method includes the use of glycerol and/or levulinic acid as a carbon source in the fermentation method.

A further object of the present invention is to provide a fermentation method for producing short-chain polyhydroxyalkanoate (PHA) biopolymers having tunable monomer compositions wherein said method includes the use of a native microorganism capable of synthesizing tunable short-chain polyhydroxyalkanoate (PHA) biopolymers from a carbon source including glycerol, levulinic acid and mixtures thereof.

A still further object of the present invention is to provide a fermentation method for producing short-chain polyhydroxyalkanoate (PHA) biopolymers wherein in said method uses a native microorganism selected from the group consisting of *Pseudomonas oleovorans, Ralstonia eutropha*, and mixtures thereof.

Another object of the present invention is to provide a fermentation method for producing short-chain polyhydroxyalkanoate (PHA) biopolymers wherein said carbon source is glycerol, glycerol plus levulinic acid, or levulinic acid with a total concentration of carbon source of approximately 1%.

Further objects and advantages of the present invention will become apparent from the following description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

For purposes of the invention, the following are definitions of certain terms to be used hereinafter.

The recitation short chain length biopolymers are biopolymers having monomeric repeat units of approximately 3-5 carbons in length.

The recitation medium chain length biopolymers are biopolymers having monomeric repeat units of approximately 6-12 carbons in length.

The recitation long chain length biopolymers are biopolymers having monomeric repeat units of approximately greater or equal to 13 carbons in length.

The term alkyl is defined as a straight chain saturated or one or more unsaturated carbon-containing chain which may be straight or branched, and can be mono or poly substituted or unsubstituted.

The term PHB is the homopolymer of poly-3-hydroxybutyrate.

The term PHB/V is the copolymer of poly-3-hydroxybutyrate-co-3-hydroxyvalerate.

The term PHV is the homopolymer of poly-3-hydroxyvalerate.

The term PHA is a general term meaning a copolymer of hydroxyacyl monomers.

The recitation tunable monomer ratios is defined as varying 3-hydroxybutyrate:3-hydroxyvalerate ratios.

Tunable PHA biopolymer properties are properties conferred based on the different ratios of glycerol and levulinic acid present as carbon sources in the fermentations.

The term tunable amount is an amount of a carbon source in any ratio of glycerol and levulinic acid which produces useable polyhydroxyalkanoate biopolymers in a microbial synthesis of polyhydroxyalkanoate biopolymers.

The terms glycerol and glycerine for purposes of the present invention are intended to be the same compound and are interchangeable.

The recitation native microorganism is a microorganism that has not been genetically engineered to improve or modify the production of PHA by the microorganism. For purposes of the present invention, the microorganism can be any microorganism capable of synthesizing polyhydroxyalkanoate biopolymers using as a carbon source an amount of glycerol, levulinic acid and mixtures thereof that drives the microbial synthesis of polyhydroxyalkanoate biopolymers.

The method uses glycerol which is a natural coproduct from the transesterification reaction in the production of biodiesel and levulinic acid (4-oxopentanoic acid) which is a promising platform chemical that can be derived from lignocellulo sic biomass via thermal hydrolysis in acid solutions and can be considered a coproduct of the pulp and paper industry. *P. oleovorans* NRRL B-14682 is used as an example of a native microorganism that can utilize both glycerol and levulinic acid for PHA polymer synthesis and the two substrates can be used alone or in combination to control the 3-HB:3-HV ratio as well as the molecular weights of the PHA polymer.

Unless defined otherwise, all technical and scientific terms used herein have the same meaning as commonly understood by one of ordinary skill in the art to which the invention belongs. The term "about" is defined as plus or minus ten percent; for example, about 100° F. means 90° F. to 110° F. Although any methods and materials similar or equivalent to those described herein can be used in the practice or testing of the present invention, the preferred methods and materials are now described.

For improvement of the production economics and the material properties of PHA biopolymers, methods for the synthesis of PHB/V copolymers with wide ranging 3-HB:3-HV ratios, the methods include the use of native microorganisms that can utilize both glycerol and levulinic acid for PHA polymer synthesis such as for example the genus *Pseudomonas*, especially *Pseudomonas oleovorans*, especially *P. oleovorans* NRRL B-14682 and the genus *Ralstonia*, especially *Ralstonia eutropha* ATCC 17699 and mixtures thereof. The methods produce PHA biopolymers which have a good balance of tensile strength and ductility.

The microorganism is cultured according to conventional methods (See for example, Brandl et al., Applied and Environmental Microbiology, Volume 54, 1977-1982, 1988; which is herein incorporated by reference in its entirety). Briefly, for shake flask production of short chain poly(hydroxyalkanoate) biopolymers, the inoculum for the shake flask production was prepared by inoculating a single approximately 50-mL Luria-Bertani (LB, 1% tryptone, 0.5% NaCl, 0.5% yeast extract) broth culture with about a 1.5-mL of P. oleovorans NRRL B-14682, by way of example, from a frozen stock culture and incubating the culture in a shake incubator at approximately 30° C. and approximately 200 rpm. After 24 hours, approximately 5-mL of the bacterial growth was transferred into 6 new separate 50-mL LB cultures and each newly inoculated culture was incubated at approximately 30° C. and approximately 200 rpm. After approximately an additional 24 hours, each of the approximately 50-mL LB flasks were aseptically harvested by centrifugation (about 8,000×g, about 20 min., approximately 4° C.) and each cell pellet resuspended in production medium from each of the respective Medium E* (composition described in Brandl et al., Applied and Environmental Microbiology, Volume 54, Pages 1977-1982, Year 1988, and reiterated below) flasks containing different glycerol:levulinic acid ratios. The entire bacterial suspensions were used as inocula for each of the 1-L production flasks. Each production flask was incubated in the shake incubator at approximately 30° C., approximately 200 rpm and 200-mL of growth media was aseptically harvested by centrifugation (conditions described above) from each flask in 24 hour intervals (up to 96 hours) and processed for polymer isolation, characterization and carbon source utilization.

For the production of short chain poly(hydroxyalkanoate) biopolymers in bench-top reactors having approximately 10-L volumes (Bioflo 3000 with a 12-L working volume, New Brunswick Scientific, Edison, N.J.) in Medium E* (starting pH approximately 7.0) containing Medium E* salts and glycerol/levulinic acid carbon sources which were autoclaved separately as concentrated solutions to sterilize and then aseptically combined into the fermentation vessel resulting in 10-L of Media E* with glycerol:levulinic acid ratios of approximately (in w/v): 1%:0, 0.75%:0.25%, 0.5%:0.5% and 0.25%:0.75%. Approximately 50-mL culture prepared as described above, was added to the 10-L fermentations as the inoculum. The fermentations were conducted at about 30° C., impeller speed of approximately 250 rpm and aeration at approximately 3 standard liters per minute (SLPM) for about 48 hours.

Sterilized Media E* contained per liter: $(NH_4)_2HPO_4$ approximately 1.1 grams; $K_2HPO_4$, approximately 5.8 grams; $KH_2PO_4$, approximately 3.7 grams. Approximately 10 milliliters of an approximately 100 mM $MgSO_4$ solution and approximately 1 ml of microelement solution were added. The microelement solution contained per liter of approximately 1N HCl, $FeSO_4.7H_2O$, approximately 2.78 grams; $MnC.4H_2O$, approximately 1.98 grams; $CoSO_4.7H_2O$, approximately 2.81 grams; $CaCl_2.2H_2O$, approximately 1.67 grams; $CuCl_2.2H_2O$, approximately 0.17 grams, and $ZnSO_4.7H_2O$, approximately 0.29 grams. The carbon source in the form of glycerol alone, different ratios of glycerol and levulinic acid, or levulinic acid alone was added to a final concentration of approximately 1%. The pH was then adjusted to approximately 6.9 to approximately 7.0 and the medium was autoclaved. For stock cultures and production cultures, the total carbon source was approximately 1% w/v. For shake flasks, the total reaction volume was approximately 1-liter using 2-L Erlenmeyer flasks. For the production of the short-chain poly(hydroxyalkanoate) biopolymers, the ratios of glycerol to levulinic acid ranged from approximately 1%:0 to approximately 0:1% respectively. One of ordinary skill in the art can readily determine which ratio to use to obtain the particular material properties of the product they desire given the detailed description of the invention. For example, for speed of production along with a maximum ductility and tensile strength using P. oleovorans, a preferred range would be between approximately 0.4% and approximately 0.6% glycerol and approximately 0.6% and 0.4% levulinic acid. On a bench top fermenter scale, the best conditions for producing the polymers with the best material properties include using a temperature of approximately 30 degrees centigrade, an impeller speed of approximately 250 rpm, aeration of approximately 3 liters per minute for approximately 48 to 72 hours using glycerol:levulinic acid ratios of approximately 0.5% to approximately 0.75% glycerol and approximately 0.5% to approximately 0.25% levulinic acid.

Glycerol and levulinic acid were used alone and in combination in the fermentative method of the invention for the synthesis of poly(3-hydroxybutyrate-co-3-hydroxyvalerate) (PHB/V) biopolymers. Shake-flask cultures of used Pseudomonas oleovorans, by way of example, and resulted in polymers containing 3-hydroxybutyrate (3-HB) and 3-hydroxyvalerate (3-HV) with tunable monomer ratios. Increased levulinic acid media content required longer culture times to achieve maximal cell productivities. Compositional analysis by $^1$H-NMR and GC/MS revealed that the use of glycerol alone resulted in poly(3-hydroxybutyrate) (PHB); however, when levulinic acid was added to the production media at concentrations of approximately ≤0.6 wt % PHB/V copolymers were produced with 3-HV contents ranging from approximately 37 to 97 mol %. A glycerol:levulinic acid substrate ratio of approximately 0.2%:0.8% resulted in poly (3-hydroxyvalerate) (PHV) but levulinic acid in the absence of glycerol resulted in no bacterial growth and consequently no polymer production. PHB, P(73%-3HB-co-27%-3HV), P(30%-3HB-co-70%-3HV) and PHV were produced using a 10-liter bench top fermentation unit molecular weights (MO of approximately $328 \times 10^3$ g/mol, $511 \times 10^3$ g/mol, $728 \times 10^3$ g/mol and $1330 \times 10^3$ g/mol, respectively. Films were solution cast from $CHCl_3$ and the tensile properties were measured at approximately 3 days and at approximately 2 months. Tensile strength remained relatively constant over time (±1.3 MPa) but elongation at break and fracture energy (toughness) both decreased for each of the polymers resulting in increased Modulus (stress÷strain) values. In each case the properties of the 3-HV-containing polymers were superior to PHB.

The following examples are intended only to further illustrate the invention.

Materials: All simple salts and reagent grade glycerol (≥99.0%) were obtained from Sigma Chemical Company (St. Louis, Mo.). Yeast extract and tryptone (components for Luria-Bertani (LB) broth) were purchased from Difco (Detroit, Mich.). Levulinic acid (98+%) was purchased from Acros Organics (Geel, Belgium). All organic solvents were HPLC grade and purchased from Honeywell Burdick and Jackson (Muskegon, Mich.) or Fisher Scientific (Fair Lawn, N.J.). The silylation reagents for GC/MS analyses including N,O-bis(trimethylsilyl)-trifluoroacetimide (BSTFA) and pyridine were purchased from Pierce (Rockford, Ill.) and Thermo Scientific (Bellefonte, Pa.), respectively.

For the following examples: *Pseudomonas oleovorans* NRRL B-14682 was used to exemplify the invention and was obtained from the National Center for Agricultural Utilization Research (NCAUR), ARS, United States Department of Agriculture, Peoria Ill. Stock cultures of the organism were prepared as described previously (Ashby, R. D., et al., Glucose/lipid mixed substrates as a means of controlling the properties of medium chain length poly(hydroxyalkanoates), Biomacromolecules, 2: 211-216 (2001)). Any native microorganism capable of synthesizing polyhydroxyalkanoate biopolymers using as a carbon source an amount of glycerol, levulinic acid and mixtures thereof that drives the microbial synthesis of polyhydroxyalkanoate biopolymers is useful in the present invention.

EXAMPLE 1

Fermentations were conducted using *Pseudomonas oleovorans* NRRL B-14682. In all cases polymer production media was Medium E* with a starting pH of approximately 7.0 (Brandl et al., 1988).

Shake flask experiments were conducted in 1-L volumes (2-L Erlenmeyer flasks) in Medium E* (Brandl, H., et al., Appl. Environ. Microbiol., 54: 1977-1982 (1988)), starting pH approximately 6.9-7.0. The initial carbon source concentration in each flask was maintained at approximately 1% (w/v). Six shake flask cultures were prepared containing the following glycerol:levulinic acid ratios (w/v): flask 1, 1%:0; flask 2, 0.8%:0.2%; flask 3, 0.6%:0.4%; flask 4, 0.4%:0.6%; flask 5, 0.2%:0.8%; flask 6, 0:1%. All media was autoclaved to sterilize. The inoculum for the shake flask experiments was prepared by inoculating a single 50-mL Luria-Bertani broth culture (LB, 1% tryptone, 0.5% NaCl, 0.5% yeast extract) with 1.5-mL of *P. oleovorans* NRRL B-14682 from a frozen stock culture and incubating the culture in a shake incubator at 30° C. and 200 rpm. After 24 hours, 5-mL of the bacterial growth was transferred into 6 new separate 50-mL LB cultures and each newly inoculated culture was incubated at 30° C. and 200 rpm. After an additional 24 hours, each of the 50-mL LB flasks were aseptically harvested by centrifugation (8,000×g, 20 min., 4° C.) and each cell pellet resuspended in production medium from each of the respective Medium E* flasks containing different glycerol:levulinic acid ratios. The entire bacterial suspensions were used as inoculum for each of the 1-L production flasks. Each production flask was incubated in the shake incubator at 30° C. and 200 rpm, and 200-mL of growth media was aseptically harvested by centrifugation (conditions described above) from each flask in 24 hour intervals (up to 96 hours) and processed for polymer isolation, characterization, and carbon source utilization as described below.

Bench-top fermentations were conducted in 10-L volumes (Bioflo 3000 with a 12-L working volume, New Brunswick Scientific, Edison, N.J.) in Medium E* (starting pH 7.0). Medium E* salts and glycerol/levulinic acid carbon source were autoclaved separately as concentrated solutions to sterilize and then aseptically combined into the fermentation vessel resulting in 10-L of Media E* with the following glycerol:levulinic acid ratios (in w/v): 1%:0, 0.75%:0.25%, 0.5%:0.5%, and 0.25%:0.75% (the 0:1% ratio was not included due to the absence of bacterial growth in shake flask experiments under those conditions). The inoculum for the 10-L fermentations was prepared by inoculating 50-mL of LB broth (content described above) with 1.5-mL of *P. oleovorans* NRRL B-14682 from a frozen stock culture and incubating the culture in a shake incubator at 30° C. and 200 rpm. After 24 h, the entire 50-mL culture was added to a 2-L Erlenmeyer flask containing 1-L of LB medium and the flask was again incubated as above. After 24 additional hours the 1-L LB culture was aseptically centrifuged (as previously described) to pellet the cells, the supernatant was discarded, and the cell pellets were resuspended in 50-mL of media from the 10-L fermentation vessel and the entire cell mass was added to the 10-L fermentation as the inoculum. The fermentations were conducted at 30° C., impeller speed of 250 rpm, and aeration at 3 standard liters per minute (SLPM) for 48 hours.

Cell growth in the shake flask experiments was monitored gravimetrically based on 1-mL and 200-mL culture aliquots that were removed at 24 hour intervals from the flasks. Three 1-mL aliquots were removed from each flask at the appropriate times, placed into separate tared Eppendorf tubes and spun at 10,000 rpm for 2 minutes at 4° C. to pellet the cells. The supernatants were combined, filtered through a 0.22-μm filter and used to determine glycerol and levulinic acid utilization by HPLC according to the procedure described below. The 200-mL aliquots were centrifuged as previously described and the cells were washed twice with deionized water, re-spun and the water fractions discarded. Cell growth in the 10-L bench-top fermentations was assessed gravimetrically solely after 48 hours post-inoculation. In all cases the cell pellets were frozen, lyophilized to dryness, weighed and used to determine cell growth over time. The volumetric cellular productivities ($Q_x$) were calculated according the Eq. (1):

$$Q_x = \frac{CDW_f - CDW_i}{t} \quad (1)$$

Where $CDW_f$ is the final cell dry weight in g/L, $CDW_i$ is the initial cell dry weight immediately following inoculation (for shake flasks the average $CDW_i$=0.12 g/L; for approximately 10-L fermentations $CDW_i$=0.19 g/L) and t is the duration of the fermentation in hours. Then the cellular yields ($Y_{x/s}$) as a function of substrate consumption were calculated according to equation 2:

$$Y_{x/s} = \frac{Q_x}{V} \quad (2)$$

Where V is the consumption rate for each substrate mixture calculated based on residual substrate concentrations over time.

Intracellular polymers from both the shake flask and bench-top experiments were isolated from the lyophilized cells by chloroform extraction at 30° C. overnight with shaking at 250 rpm. Cellular debris was removed by filtration through Whatman #2 filter paper and the chloroform evaporated from the filtrate to give the crude polymers. Each crude polymer was redissolved in a small volume of chloroform and precipitated a total of 3 times by dropwise addition to cold methanol. The polymer was recovered, placed into a tared vial, dried in vacuo for 24 h and weighed to determine polymer yield. The volumetric polymer productivities ($Q_p$) were calculated according to equation 3:

$$Q_p = \frac{PY_f - PY_i}{t} \quad (3)$$

Where $PY_f$ is the final polymer yield in g/L, $PY_i$ is the initial polymer yield at inoculation which was zero for both shake flasks and 10-L fermentations and t is the duration of the fermentation in hours. Then, polymer yields ($Y_{p/s}$) as a function of substrate consumption were calculated according to equation 4.

$$Y_{p/s} = \frac{Q_p}{V} \quad (4)$$

Repeat unit compositions were determined by Proton—Nuclear Magnetic Resonance Spectroscopy ($^1$H-NMR) and Gas Chromatography/Mass Spectrometry (GC/MS) of the trimethylsilyl derivatives of the 3-hydroxymethyl esters. Solution-state NMR spectra were recorded at 9.4 Tesla on a Varian INOVA NMR Spectrometer, using a 5-mm dual broadband probe with z-axis pulsed field gradients operating at 20° C. All samples were dissolved in deuterated chloroform (CDCl$_3$) with tetramethylsilane (TMS) added as an internal $^1$H reference. The $^1$H (proton) spectra, at 400 MHz, had a sweep-width of 4500 Hz, were acquired with a 90-degree pulse angle and a 1 second relaxation delay.

Samples for GC/MS analysis were prepared according to Brandl et al. (Brandl, H., Appl. Environ. Microbiol., 54: 1977-1982 (1988)) and were silylated by reacting 10-μL of each sample with 250-μL BSTFA and 200-μL pyridine. The mixtures were heated at 75° C. for 25 min and allowed to cool to room temperature. Finally, 150-μL of hexane was added to each sample and the samples were analyzed by GC/MS as previously described (Ashby, R. D., et al., Int. J. Biol. Macromol. 27: 355-361 (2000)). Percent composition was obtained from the $^1$H-NMR analyses by peak integration and from the GC/MS analyses by reconstructing the chromatograms selecting the 175 ion, indicative of silylated 3-hydroxymethyl esters, and identifying the molecular ion (M)-15 amu (CH$_3$ group), M-31 amu (CH$_2$OH group) and M-73 (trimethylsilyl group) as described by Lee and Choi (Lee, E. Y., and C. Y. Choi, J. Ferm. Bioengin., 80: 408-414 (1995)).

Molecular weight averages were determined by gel permeation chromatography (GPC). Number average Molecular weight ($M_n$) and weight average Molecular weight ($M_w$) of the polymers were determined using an LC-20AD Liquid Chromatograph equipped with a SIL-20A auto-sampler and RID-10A refractive index detector (Shimadzu, Japan) as described previously (Zhu, C., et al., Biotechnol. Prog., 26: 424-430 (2010)). Briefly, the polymers were dissolved in chloroform at a final concentration of 0.7 mg/mL and the resulting polymer solution was filtered (PTFE membrane, 0.22-μm) before analysis. An SDV 8×300 mm column with 5-μm porosity was used (Polymer Standards Service, USA) with an oven temperature of 40° C. The mobile phase was CHCl$_3$ with a flow rate of 1 mL/min. Standard curves were created using polystyrene standards with a range from 682 to 1,670,000 g/mol and low polydispersities (Polystyrene High Mw Standards Kit, Polymer Standards Service, USA). The molecular weights of the polymers were calculated relative to these standards.

Glycerol and levulinic acid utilization was determined by High Performance Liquid Chromatography (HPLC). Culture supernatants were filtered through a 0.22-μm filter and placed in an auto sampler vial. An Agilent 1200 series HPLC equipped with an ion exclusion column (Aminex HPX-87H, Bio-Rad, Hercules, Calif.) at 60° C. and a refractive index detector was used to analyze each sample. A 5-μL injection was eluted at 0.6 mL/min with 5 mM sulfuric acid prepared in HPLC-grade water. Data were processed and analyzed using the Agilent ChemStation software. The HPLC was calibrated with standards containing glycerol and levulinic acid. Standards were verified with a secondary standard after every 10 samples. Each sample was injected twice and the results for each sample were averaged.

Thermal properties were determined using a Perkin Elmer Pyris 1 (Norwalk, Conn.) differential scanning calorimeter (DSC) at a heating rate of 10° C./min with a dry nitrogen purge. The instrument was calibrated using both indium ($T_m=156°$ C.) and cyclohexane (with transition temperatures at $-87°$ C. and 6° C.). Between 5-10 mg of polymer sample was accurately weighed and placed into sealed aluminum sample pans and heated from $-40°$ to 200° C. Each sample was then held at 200° C. for 2 minutes and then cooled back to $-40°$ C. at 10° C./min. The glass transition temperatures ($T_g$) and melting temperatures ($T_m$) were determined from the original heat and were taken as midpoint and peak temperatures of the melting endotherms, respectively. The crystallization temperatures ($T_c$) were determined from the exotherms derived from the cooling cycle.

Tensile property measurements included tensile strength (MPa), elongation at break (%), Young's Modulus (MPa), and fracture energy (J/cm$^3$). An upgraded Instron mechanical property tester, model 1122 (Instron, Norwood, Mass.), and Testworks-4 data acquisition software (MTS Systems Corp., Minneapolis, Minn.) were used throughout the studies. Properties were measured with a sample length of approximately 2 cm between two grips. The strain rate (crosshead speed) was set at approximately 5 cm/min. All samples were tested in a conditioning room set at approximately 23±2 degrees C. and approximately 50±5% relative humidity.

Figure 1A:
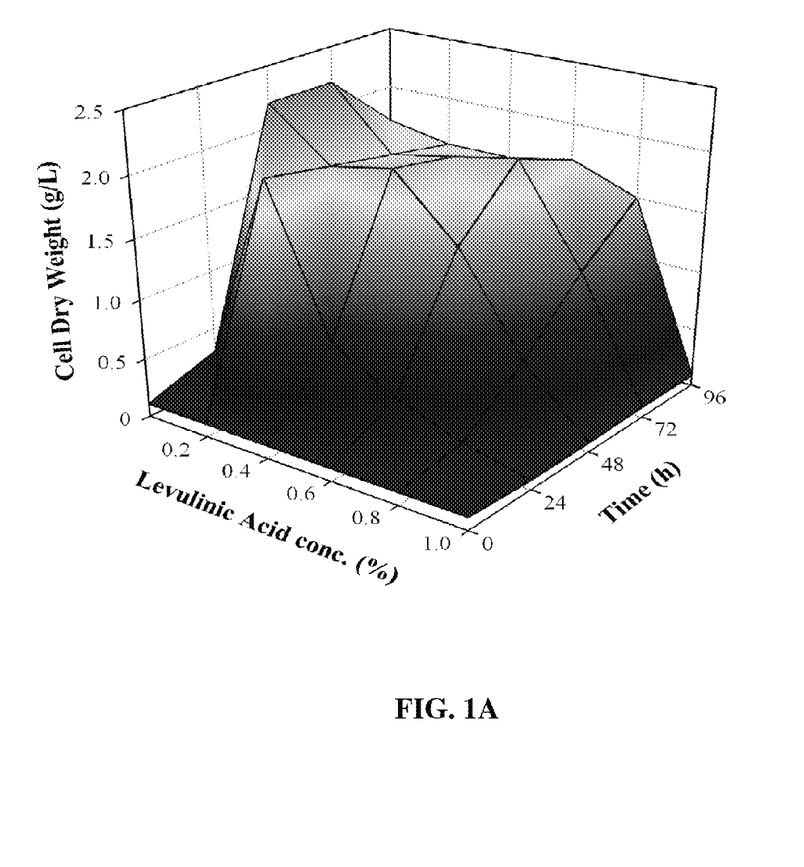
FIGS. 1A-1C are graphs showing cell yields (A), PHA polymer yields (B), and cell productivity (C) in shake flask culture as a function of starting levulinic acid media concentration and time. Note: the total carbon source concentration in each flask was approximately 1% (w/v) and the difference between the starting levulinic acid media concentration and 1% was made up with glycerol.
Figure 1B:
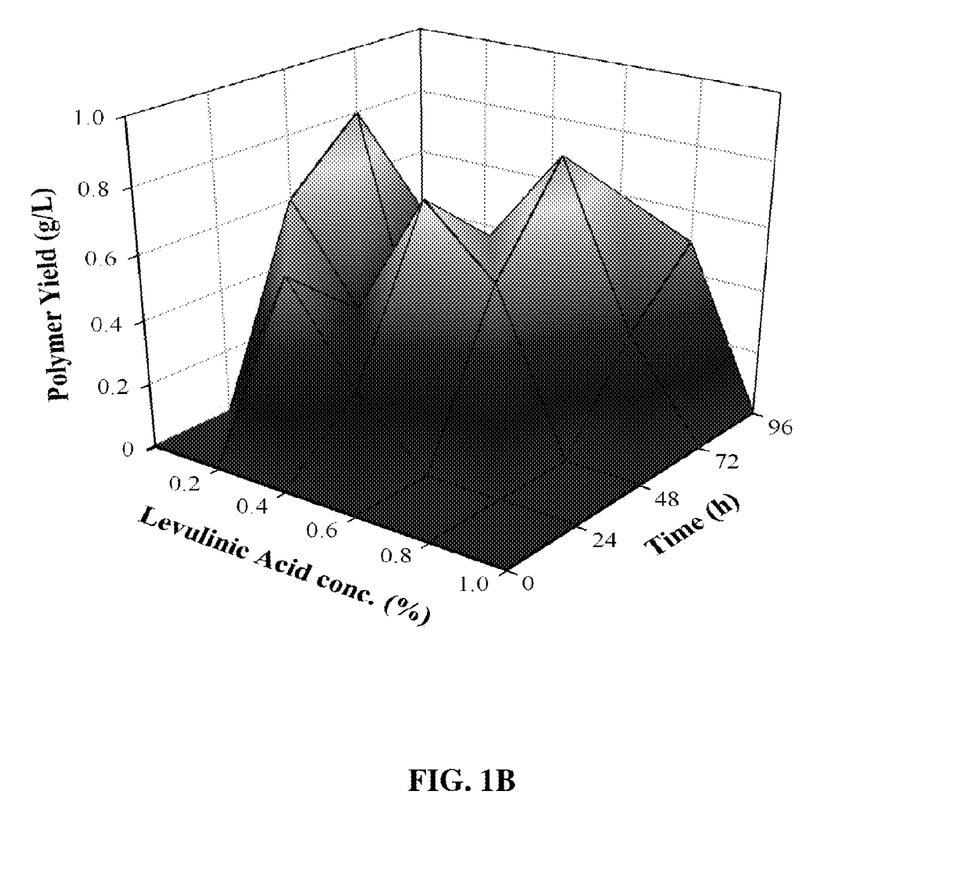
Figure 1C:
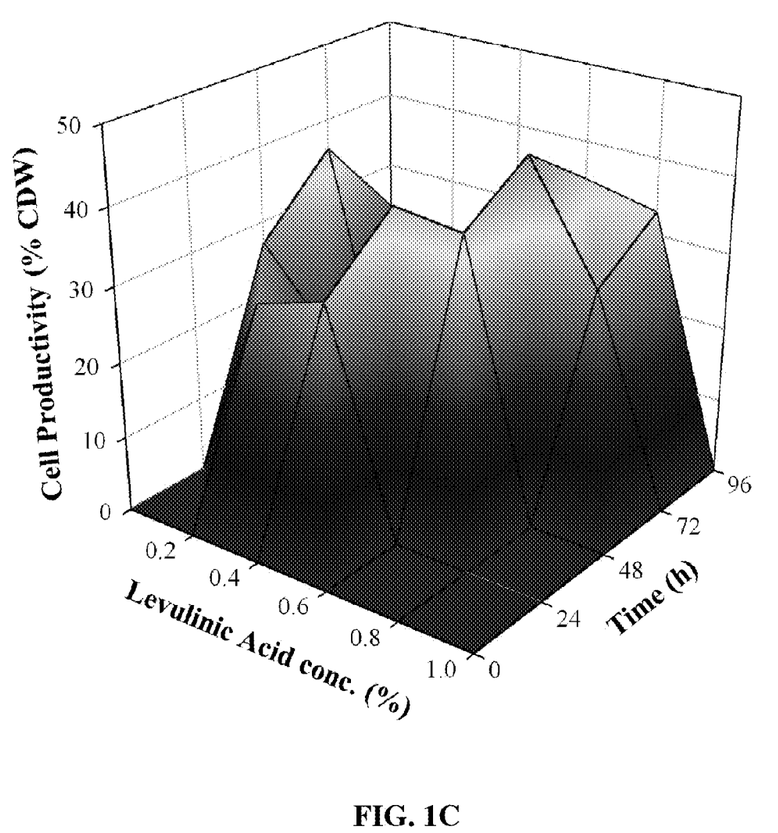

Shake-flask cultures (1% total carbon source concentration) were used to establish the feasibility of using glycerol and levulinic acid to produce PHA biopolymers. Different ratios of glycerol and levulinic acid were combined and used as substrates for PHA biosynthesis and the results for cell yield, PHA yield, and cellular productivity [(polymer yield÷cell yield)×100] can be seen in FIGS. 1A-1C, respectively. Trends showed that increasing concentrations of levulinic acid in the media necessitated longer culture times in order to reach maximum cell and PHA yields. In the absence of levulinic acid (1% glycerol) maximum cell and PHA yields occurred at about 72 hours indicating that levulinic acid was beneficial in initiating cell growth at relatively small concentrations. The cell and maximum PHA yields for each substrate ratio are reported in Table 1. Glycerol alone resulted after 72 h in a maximum cell dry weight (CDW) and polymer yield (PY) of 2.2 g/L and 0.8 g/L, respectively after 72 hours with a substrate consumption rate (V) of approximately 0.13 $h^{-1}$. In contrast, levulinic acid alone resulted in no bacterial growth or polymer production throughout the entire 96 h experiment (See FIGS. 1A and 1B, respectively). The collective use of glycerol and levulinic acid as co-substrates did result in polymer synthesis and in fact the inclusion of up to approximately 0.4 wt % levulinic acid actually reduced the time necessary to reach maximum cell density and polymer yields when compared to glycerol alone. V values remained relatively constant at approximately 0.13-0.14 $h^{-1}$ up to 0.6 wt % levulinic acid but then tailed off to approximately 0.10 at a levulinic acid concentration of approximately 0.8 wt %. In addition, higher levulinic acid contents resulted in reduced volumetric cellular ($Q_x$) and PHA polymer ($Q_p$) productivities and also lowered the cellular ($Y_{x/s}$) and PHA polymer ($Y_{p/s}$) yields as a function of substrate consumption. This demonstrated that although *P. oleovorans* NRRL B-14682 can utilize glycerol and levulinic acid together for growth and polymer synthesis, the growth rates are retarded and polymer synthesis is slowed as the levulinic acid contents elevate. Maximum cell productivities as a function of starting glycerol:levulinic acid media concentration and time ranged from approximately 26% to approximately 42% in the shake-flask cultures depending on the co-substrate ratio. As the levulinic acid media content increased, longer times were required to achieve maximum CDW and PY. For example, a starting co-substrate ratio of 0.8% glycerol and 0.2% levulinic acid resulted in a maximum CDW of 1.9 g/L and a maximum PY of 0.3 g/L after 24 h. As the glycerol:levulinic acid ratio varied to 0.6%:0.4%, 0.4%:0.6% and 0.2%:0.8%, 48 h (CDW=1.9 g/L, PY=0.5 g/L), 72 h (CDW=1.9 g/L, PY=0.6 g/L) and 96 h (CDW=1.5 g/L, PY=0.3 g/L) were required to achieve maximum CDW and PY, respectively.

The monomer content of the polymers derived from the shake flask cultures were determined by GC/MS. Table 2 shows the results of those determinations. Previous reports have documented that glycerol alone results in PHB homopolymers when *P. oleovorans* NRRL B-14682 is used (Ashby et al., 2011). In this study, the polymers isolated from the 1% glycerol flask at 48 h through 96 h were composed entirely of 3-hydroxybutyrate (3-HB) monomers. Interestingly, at glycerol:levulinic acid ratios of 0.8%:0.2% and 0.6%:0.4% PHB/V copolymers were produced with significant 3-HB and 3-HV monomer fractions. In both instances the 3-HB:3-HV ratios increased with the shake-flask duration. At 96 h no polymer was isolated due to the complete utilization of carbon substrates; see Table 3 and the tendency of PHA-producing bacterial strains to metabolize these stored polymers for survival in carbon deficient environments. The 3-HB:3-HV ratio (calculated by the 3-HB monomer content÷3-HV monomer content) increased from 0.28 to 1.70 between 24 h and 72 h for the shake-flask containing a glycerol:levulinic acid ratio of 0.8%:0.2% and from 0.05 to 0.72 between 24 h and 72 h for the shake-flask containing a starting glycerol:levulinic acid ratio of 0.6%:0.4%. The polymers derived from the flasks containing glycerol:levulinic acid ratios of 0.4%:0.6% and 0.2%:0.8% were composed primarily of 3-HV monomers. In fact, the 48 h culture from the 0.4%:0.6% glycerol:levulinic acid flask as well as all of the polymer recovered from the 0.2%:0.8% glycerole:levulinic acid flask were determined to be solely poly(3-hydroxyvalerate) (PHV) while the polymers derived from the 0.4%:0.6% glycerol:levulinic acid flask at 72 h and 96 h were determined to contain >95 mol % 3-HV.

The compositional results for the polymers produced in shake-flask culture seem to correlate to the relative utilization rates of glycerol and levulinic acid in the media. Table 3 shows the relative glycerol and levulinic acid concentrations in the media over time. By calculating percent loss for both glycerol and levulinic acid, it was determined that at initial glycerol concentrations between 0.4% and 1.0%, glycerol utilization was confined to 14-15% of the starting material between 0 and 24 h. In contrast, cultures containing relatively small levulinic acid concentrations (0.2% and 0.4%) demonstrated utilization for the levulinic acid even when higher concentrations of glycerol were available. In fact, data showed that at starting glycerol:levulinic acid ratios of 0.8%:0.2% and 0.6%:0.4% the levulinic acid media concentrations decreased by 100% and 38%, respectively after 24 h but at the inverse ratios of 0.2%:0.8% and 0.4%:0.6% glycerol:levulinic acid, the glycerol was present until 72 h post-inoculation. The cultures containing between 0.2% and 0.6% levulinic acid show almost complete utilization of the levulinic acid substrate by 48 h while glycerol concentrations do not show greater than 80% utilization until 72 h. In the culture containing 0.2% glycerol and 0.8% levulinic acid, the levulinic acid begins to show its toxic effects on the bacterium by reducing the rates of cell growth and carbon source utilization. In fact, in this culture 31% of the levulinic acid remained after 72 h. Interestingly, because the composition of the polymers derived from the shake-flask containing a 0.2%:0.8% glycerol:levulinic acid ratio were composed entirely of 3-HV, it appeared that this bacterial strain required a co-substrate to initiate cell growth (glycerol in this case) but once growing, effectively utilized levulinic acid for polymer production.

Scale-up to 10-L bench-top fermentations was conducted to generate sufficient polymers to assess their mechanical and tensile properties. At the 10-L scale, 4 different glycerol:levulinic acid co-substrate ratios were used. They were (in w/v) 1%:0, 0.75%:0.25%, 0.5%:0.5% and 0.25%:0.75%. In all cases the CDW and PY increased at the 10-L scale compared to shake-flask cultures (Table 1). The fermentations containing 1% glycerol, 0.75%:0.25% and 0.5%:0.5% glycerol:levulinic acid all showed CDW values ranging from 2.3 to 2.7 g/L and PY's of 1.1 to 1.2 g/L resulting in cell productivities of 41% to 48% of the CDW. In contrast, the fermentation containing 0.25%:0.75% glycerol:levulinic acid only reached a CDW of 2.0 g/L and a PY of 0.7 g/L, a cell productivity of 35%. The $Q_x$ and $Q_p$ values remained relatively constant ($Q_x$=0.04-0.05; $Q_p$=0.01-0.03) regardless of the starting glycerol:levulinic acid ratio however the $Y_{x/s}$ and $Y_{p/s}$ values decreased by 35% and 43%, respectively as the levulinic acid concentration increased in the media. These results further demonstrated the detrimental effects of elevated levulinic acid concentrations on the rate of substrate utilization for cell growth and polymer production.

The polymers that were produced from the 10-L fermentations were analyzed by $^1$H-NMR (see FIG. 4) and GC/MS for monomer content. The polymer derived from 1% glycerol and no levulinic acid showed typical $^1$H-NMR resonances for PHB [in ppm; 1.22 (doublet, d, CH$_3$), 2.47 (multiplet, m, —CH$_2$—), 5.19 (m, —CH—)] while the polymer derived from the culture containing the 0.25%:0.75% ratio of glycerol:levulinic acid showed resonances characteristic of PHV [in ppm; 0.83 (triplet, t, CH$_3$), 1.59 (m, —CH$_2$—CH$_3$), 2.47 (m, backbone —CH$_2$—), 5.02 (m, —CH—)]. The polymers derived from the cultures containing 0.75%:0.25% and 0.5%:0.5% glycerol:levulinic acid ratios both showed resonances characteristic of PHB/V copolymers [in ppm; 0.83 (t, 3-HV sidechain CH$_3$), 1.22 (d, 3-HB sidechain CH$_3$), 1.59 (m, 3-HV sidechain —CH$_2$—CH$_3$), 2.47 (m, 3-HB and 3-HV backbone —CH$_2$—), 5.02 (m, 3-HV backbone —CH—CH$_2$—CH$_3$), 5.19 (m, 3-HB backbone —CH—CH$_3$)]. By comparing the integration values of the resonances at 1.22 ppm and 1.59 ppm and also those of the resonances at 5.02 ppm and 5.19 ppm we determined the ratio of 3-HB to 3-HV in each copolymer, then by averaging these values with those obtained from GC/MS (data not shown) we determined the polymer compositions from the 4 10-L fermentations. The results of these determinations are shown in Table 4.

Figure 3A:
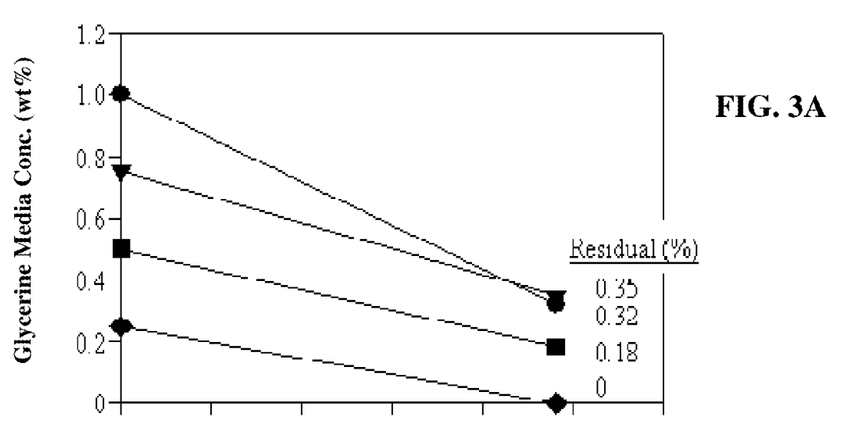
FIGS. 3A and 3B are graphs showing comparative glycerol (A) and levulinic acid (B) utilization in the 10-L fermentations containing glycerol:levulinic acid ratios of 1%:0 (•), 0.75%:0.25% (▼), 0.5%:0.5% (■) and 0.25%:0.75% (♦) as described below.
Figure 3B:
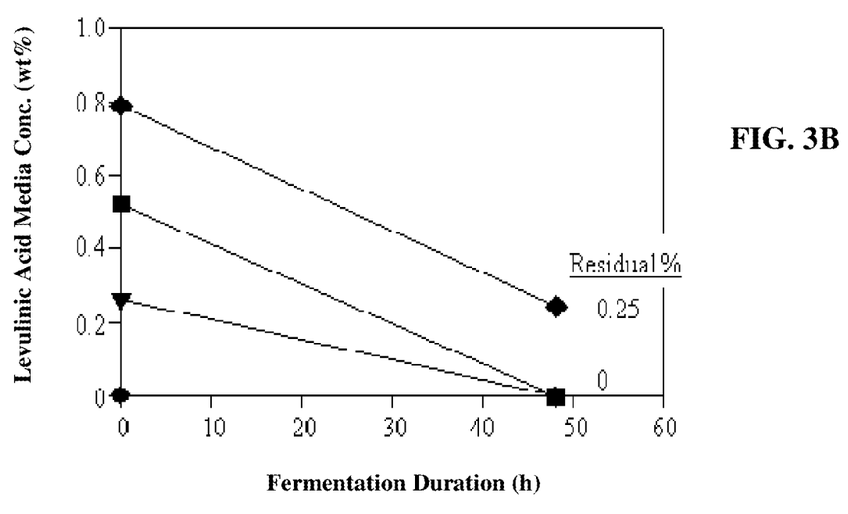
Figure 4:
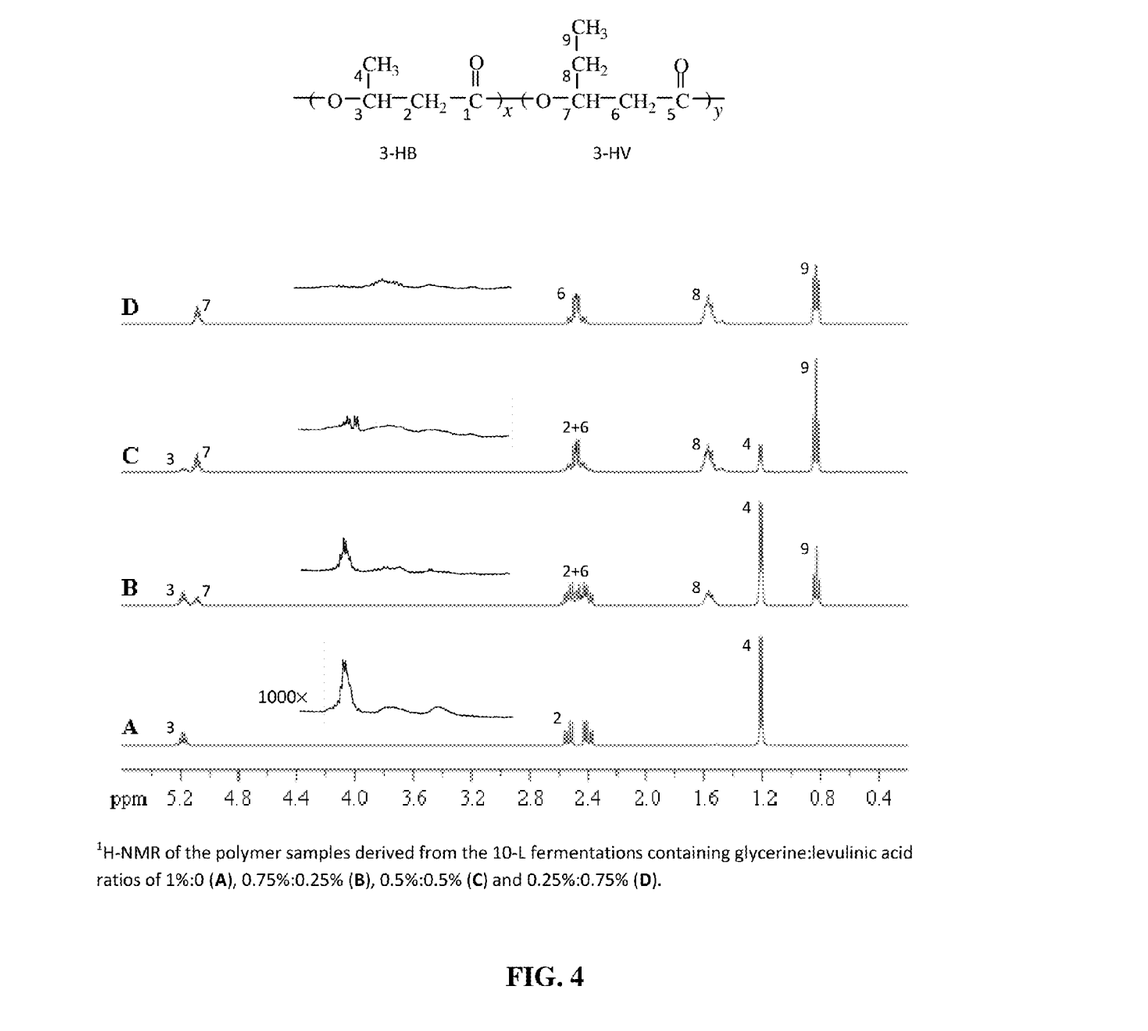
FIGS. 4A-4D are graphs of $^1$H-NMR of the polymer samples derived from the 10-L fermentations containing glycerol:levulinic acid ratios of approximately 1%:0 (A), approximately 0.75%:0.25% (B), approximately 0.5%:0.5% (C), and approximately 0.25%:0.75% (D).

FIG. 3 shows the graphs of glycerol (FIG. 3A) and levulinic acid (FIG. 3B) utilization in each of the 4 fermentations. In all cases the majority (if not all) of each carbon source was utilized by the organism by 48 h. The magnitude of the slopes (m) of the lines in the figures help to better understand the relative rates of carbon source utilization relative to each other so long as the concentrations did not go to 0. In the absence of levulinic acid the glycerol concentration decreased by 68% (m=−0.48). As levulinic acid was introduced into the media the rate of glycerol utilization decreased by 46% (m=−0.26) and 50% (m=−0.24) for the cultures with starting carbon source ratios of 0.75%:0.25% and 0.5%:0.5% glycerol:levulinic acid, respectively. These results corresponded with increased levulinic acid utilization. The only fermentation that showed any residual levulinic acid after 48 h was the fermentation that began with a glycerol:levulinic acid ratio of 0.25%:0.75%. Unfortunately, that same fermentation showed no residual glycerol after 48 h making a comparison of the average rate of carbon source utilization (based on slope values) in that fermentation impossible. It was decided that the best fermentation for determining the comparative rate of glycerol vs. levulinic acid utilization was the fermentation that began with a carbon source ratio of 0.5%:0.5%. Starting with the same concentration of each carbon source makes the comparison easier and although the concentration of levulinic acid did go to 0 within 48 h, the data from the shake-flask cultures (Table 2) showed no residual levulinic acid in the 0.6%:0.4% culture after 48 h and only a small amount (0.14%) of levulinic acid remaining in the 0.4%:0.6% culture after 48 h. Based on this data it was determined that the 0.5%:0.5% culture would be the best comparative representation of glycerol vs. levulinic acid utilization. By comparing the slopes of the lines for glycerol (m=−0.24) and levulinic acid utilization (m=−0.46) in the 0.5%:0.5% fermentation, it was concluded that levulinic acid was utilized faster than glycerol which corroborates the data from the shake-flask cultures and better explains the higher 3-HV content in the polymers at shorter fermentation times. In fact, upon compositional analysis of the polymer derived from the glycerol:levulinic acid substrate ratio of 0.5%:0.5% (see below) it was found that the 3-HB:3-HV ratio was 1:2.3, comparable to the relative utilization rates of glycerol to levulinic acid (1:1.9) calculated from the slope values above.

Previous reports have shown that glycerol tends to act as a chain terminating agent during PHA polymer synthesis, thus causing a reduction in molecular weight (Zhu, C., et al., Biotechnol. Prog., 26: 424-430 (2010); Ashby, R. D., et al., Biomacromolecules, 6: 2106-2112 (2005)). The magnitude of these reductions is based on the glycerol concentration in the media, the more glycerol there is present the higher the likelihood of a chain terminating reaction resulting earlier in the polymerization process resulting in smaller molecular weight polymers. This was certainly the case in this study. Molecular weight data is shown in Table 4. It is evident that the molecular weights decreased as the starting glycerol media concentration increased regardless of the monomer content. In prior papers showing molecular weight decreases with glycerol, the authors showed covalent bonding between glycerol and the polymer chain by $^1$H-NMR (Zhu, C., et al., Biotechnol. Prog., 26: 424-430 (2010); Ashby, R. D., et al., Biomacromolecules, 6: 2106-2112 (2005)). The resonances corresponding to these chain-terminating reactions were also present in the $^1$H-NMR results in this study at 4.1 ppm (see FIG. 4) whose intensity increased as the glycerol concentration increased indicating a larger concentration of glycerol-terminated polymer chains and reduced molecular weights.

TABLE 1

Maximum values for cell dry weight and PHA polymer yield as a function of varying glycerol:levulinic acid ratios and durations at the 1-L shake flask and 10-L bench-top fermentation scale.

| Glycerol:Levulinic acid Ratio[a] | Duration (h) | $V^b$ (h$^{-1}$) | CDW (g/L) | $Q_x$ | $Y_{x/s}$ | PY (g/L) | $Q_p$ | $Y_{p/s}$ | Productivity (% CDW) |
|---|---|---|---|---|---|---|---|---|---|
| Shake Flevulinic acidsks: | | | | | | | | | |
| 1.0%:0 | 72 | 0.13 | 2.2 | 0.03 | 0.23 | 0.8 | 0.01 | 0.09 | 36 |
| 0.8%:0.2% | 24 | 0.13 | 1.9 | 0.07 | 0.57 | 0.5 | 0.02 | 0.16 | 26 |

TABLE 1-continued

Maximum values for cell dry weight and PHA polymer yield as a function of varying glycerol:levulinic acid ratios and durations at the 1-L shake flask and 10-L bench-top fermentation scale.

| Glycerol:Levulinic acid Ratio[a] | Duration (h) | $V^b$ ($h^{-1}$) | CDW (g/L) | $Q_x$ | $Y_{x/s}$ | PY (g/L) | $Q_p$ | $Y_{p/s}$ | Productivity (% CDW) |
|---|---|---|---|---|---|---|---|---|---|
| 0.6%:0.4% | 48 | 0.14 | 1.9 | 0.04 | 0.26 | 0.7 | 0.01 | 0.10 | 37 |
| 0.4%:0.6% | 72 | 0.14 | 1.9 | 0.02 | 0.18 | 0.8 | 0.01 | 0.08 | 42 |
| 0.2%:0.8% | 96 | 0.10 | 1.5 | 0.01 | 0.14 | 0.5 | 0.005 | 0.05 | 33 |
| 10-L Fermentations: | | | | | | | | | |
| 1%:0 | 48 | 0.14 | 2.7 | 0.05 | 0.37 | 1.1 | 0.02 | 0.16 | 41 |
| 0.75%:0.25% | 48 | 0.14 | 2.3 | 0.04 | 0.31 | 1.1 | 0.02 | 0.16 | 48 |
| 0.5%:0.5% | 48 | 0.17 | 2.6 | 0.05 | 0.30 | 1.2 | 0.03 | 0.15 | 46 |
| 0.25%:0.75% | 48 | 0.16 | 2.0 | 0.04 | 0.24 | 0.7 | 0.01 | 0.09 | 35 |

[a]All glycerine:levulinic acid ratios are given in w/v.
[b]Specific consumption rate (V) for the substrates was determined from the slope of the line relating residual substrate concentration to time.

TABLE 2

PHA polymer compositions based on initial glycerol:levulinic acid media concentration ratios and time at the shake-flask scale.

| Initial Glycerol:Levulinic acid ratio[a] | Incubation Time (h) | Monomer Content[b] (mol %) | |
|---|---|---|---|
| | | 3-HB | 3-HV |
| 1.0%:0 | 24 | No Polymer Recovered | |
| | 48-96 | 100 | 0 |
| 0.8%:0.2% | 24 | 22 | 78 |
| | 48 | 59 | 41 |
| | 72 | 63 | 37 |
| | 96 | No Polymer Recovered | |
| 0.6%:0.4% | 24 | 5 | 95 |
| | 48 | 22 | 78 |
| | 72 | 42 | 58 |
| | 96 | No Polymer Recovered | |
| 0.4%:0.6% | 24 | No Polymer Recovered | |
| | 48 | 0 | 100 |
| | 72-96 | 3-4 | 96-97 |
| 0.2%:0.8% | 24 | No Polymer Recovered | |
| | 48-96 | 0 | 100 |
| 0:1.0% | 24-96 | No Polymer Recovered | |

[a]All initial glycerol:levulinic acid ratios are given in w/v.
[b]Monomer contents for shake flask experiments were determined by GC/MS.

TABLE 3

Glycerol and levulinic acid utilization[a] by *P. oleovorans* NRRL B-14682 based on initial glycerol:levulinic acid media concentration ratios and time at the shake-flask scale.

| Initial Glycerol:Levulinic Acid Ratios[b] | 24 Hours[c] | | 48 Hours[c] | | 72 Hours[c] | | 96 Hours[c] | |
|---|---|---|---|---|---|---|---|---|
| | Glycerol | Levulinic Acid | Glycerol | Levulinic Acid | Glycerol | Levulinic Acid | Glycerol | Levulinic Acid |
| 1.0%:0 | 0.86 | 0 | 0.36 | 0 | 0.08 | 0 | 0 | 0 |
| 0.8%:0.2% | 0.69 | 0 | 0.36 | 0 | 0.14 | 0 | 0 | 0 |
| 0.6%:0.4% | 0.51 | 0.25 | 0.31 | 0 | 0.10 | 0 | 0 | 0 |
| 0.4%:0.6% | 0.34 | 0.53 | 0.16 | 0.14 | 0.02 | 0 | 0 | 0 |
| 0.2%:0.8% | 0.18 | 0.78 | 0.05 | 0.59 | 0 | 0.25 | 0 | 0 |
| 0:1.0% | 0 | 1.00 | 0 | 1.00 | 0 | 1.00 | 0 | 1.00 |

[a]Relative glycerol and levulinic acid utilization was determined by HPLC (see Materials and Methods section for details).

[b]All glycerol and levulinic acid values are based on averages of weight percentages (n = 3).

[c]Time intervals correspond to shake-flask

TABLE 4

Polymer compositions, molecular weights and thermal properties of the sc-PHA polymers derived from 10-L bench-top batch fermentations in the presence of varying ratios of glycerol and levulinic acid.

| | Compositions[b] | | Molecular Weights[c] | | Thermal Properties[d] | | | | |
|---|---|---|---|---|---|---|---|---|---|
| Sample #[a] | 3-HB | 3-HV | $M_n$ (×10³) | | | | | | |
| (Film age) | (mol %) | (mol %) | (g/mol) | $M_w/M_n$ | $T_m$ (° C.) | $\Delta H_m$ (J/g) | $T_c$ (° C.) | $\Delta H_c$ (J/g) | $T_g$ (° C.) |
| 1; (3 days) | 100 | 0 | 328 | 1.92 | 173 | 80.0 | 95 | −57.4 | 3 |
| (2 mos.) | | | | | 172 | 90.9 | 84 | −57.5 | 3 |
| 2; (3 days) | 73 | 27 | 511 | 1.97 | 99 | 3.8 | — | — | −1 |
| (2 mos.) | | | | | 97 | 9.5 | 2 | −6.5 | −2 |
| 3; (3 days) | 30 | 70 | 728 | 1.98 | 103 | 34.9 | −4 | −10.2 | −15 −5 |
| (2 mos.) | | | | | 102 | 38.7 | −5 | −8.1 | −16 −5 |
| 4; (3 days) | 0 | 100 | 1330 | 1.52 | 108 | 54.2 | −12 | −12.7 | −16 |
| (2 mos.) | | | | | 106 | 59.2 | −12 | −9.2 | −16 |

[a]Samples 1-4 were produced from initial glycerol:levulinic acid ratios (in wt %) of 1.0:0, 0.75:0.25, 0.5:0.5 and 0.25:0.75, respectively.
[b]Compositions were determined immediately after synthesis by GC/MS and ¹H-NMR; 3-HB = 3-hydroxybutyrate, 3-HV = 3-hydroxyvalerate.
[c]Molecular weights were determined immediately after synthesis by GPC; $M_n$ = number average moleclar weight, $M_w/M_n$ = polydispersity.
[d]Thermal properties were determined by DSC on film samples that were solution cast from $CHCl_3$ and aged for 3 days and 2 months; $T_m$ = melting temperature, $\Delta H_m$ = heat of fusion, $T_c$ = crystallization temperature, $\Delta H_c$ = heat of crystallization, $T_g$ = glass transition temperature.

EXAMPLE 2

Solution cast films were prepared from each of the 4 polymers derived from the 10-L bench-top fermentations in Example 1. Each thin film was tested for three days and after two months. Five hundred milligrams of each polymer was weighed and added to a 25-mL beaker after which 15-mL of $CHCl_3$ was added to each beaker and the contents allowed to dissolve completely. Once dissolved, the mixtures were poured into separate aluminum dishes (7.5 cm dia.) and the chloroform allowed to evaporate off at room temperature. The resulting polymer films were then placed under vacuum overnight to thoroughly remove any residual solvent. The resulting films were 0.11±0.02 mm thick and were cut into strips 7 mm wide in preparation for tensile testing (described below). Films were held at room temperature and 50% relative humidity prior to testing at 3 days and 2 months post-casting.

Tensile property measurements included tensile strength (MPa), elongation at break (%), Young's Modulus (MPa), and fracture energy (J/cm³). Tensile strength is the stress in tension that is required to fracture the polymer films. Fracture energy is defined as the energy needed to fracture the polymer film samples, this physical quantity is sometimes referred to as "toughness." An upgraded Instron mechanical property tester, model 1122 (Instron, Norwood, Mass.), and Testworks-4 data acquisition software (MTS Systems Corp., Minneapolis, Minn.) were used throughout this work. Properties were measured with a sample length of 2 cm between the two grips. The strain rate (crosshead speed) was set at 5 cm/min. All samples were tested in a conditioning room set at 73±3° C. and 50±5% relative humidity.

The results are shown in Table 5. Based on these results, it was evident that the aged polymers derived from glycerol and levulinic acid exhibited mechanical/tensile properties that compared favorably to previously published results (Doi, Microbial polyesters, VCH Publishers, New York, 1990; Chen, Production and applications of microbial polyhydroxyalkanoates, In: Chiellini, E., Solevulinic acidro, R. (Eds.), Biodegradable Polymers and Plastics. Kluwer Academic/Plenum Publishers, New York, pp. 155-166, 2003). However, there were minor decreases in the tensile strength and modulus and slight increases in the elongation to break values which could be attributed to smaller molecular weights brought about by glycerol-based end-capping. When compared to each other, the mechanical/tensile property results for the current polymers showed that tensile strength was higher in the PHB homopolymer compared to the 3-HV containing polymers and that aging had little effect on the tensile strength of any of the polymers. These same trends were not seen in elongation at break and fracture energy. Aging had a dramatic reductive effect on elongation at break and also fracture energy, which is a measure of a material's "toughness." Although these parameters reduced over time, the properties of the 3-HV containing polymers remained superior to the PHB homopolymer regardless of the 3-HV content, and although the 3-HV content is important for property control, the increased molecular weights of the 3-HV-containing polymers undoubtedly also played a role in their superior properties compared to PHB. Based on the results of the tensile property measurements, it appeared that the PHB/V polymers containing 73 mol % 3-HB and 27 mol % 3-HV exhibited superior properties compared to the other polymers tested.

These same films were tested by DSC to determine the effects of aging on the thermal properties of the polymers. The results are shown in Table 4. Previous reports have shown that PHB/V exhibits isodimorphic behavior, and 3-HV contents of around 40 mol % result in minimum melting temperatures and enthalpies of fusion ($\Delta H_m$) because of a changeover from the PHB lattice to the PHV lattice (Bluhm et al., 1986, Pearce and Marchessault 1994). This was the case for the polymers in this study. The PHB/V polymer containing 27 mol % 3-HV showed a melting temperature ($T_m$) value of 99° C. ($\Delta H_m$=3.8 J/g), while the PHB/V polymer containing 70 mol % 3-HV and the PHV homopolymer showed $T_m$ values of 103° C. ($\Delta H_m$=34.9 J/g) and 108° C. ($\Delta H_m$=54.2

Figure 2A:
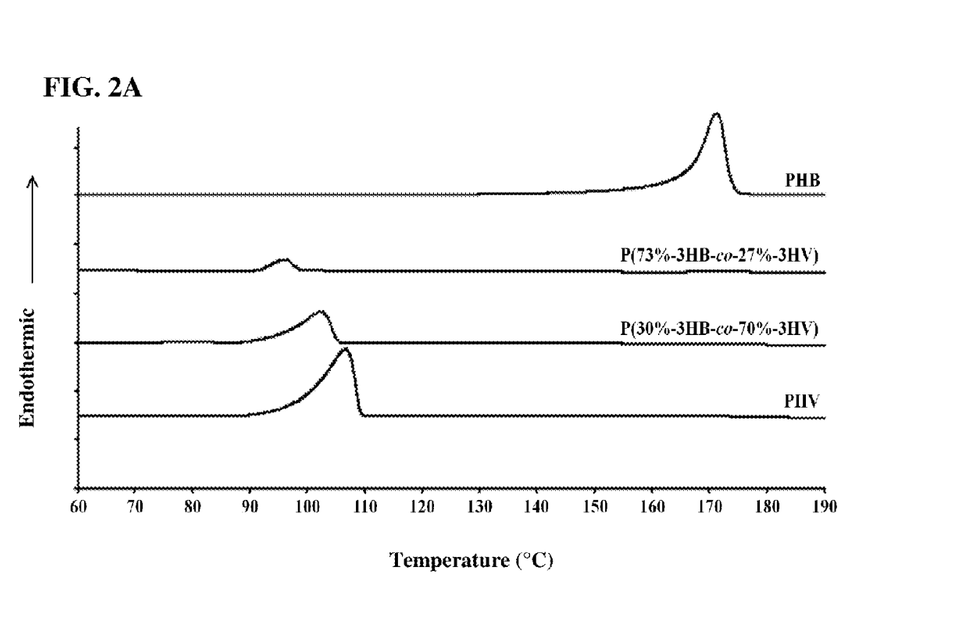
FIGS. 2A and 2B are graphs showing DSC traces of melt (A) and glass transition (B) endotherms from the polymers derived from the 10-L fermentations.
Figure 2B:
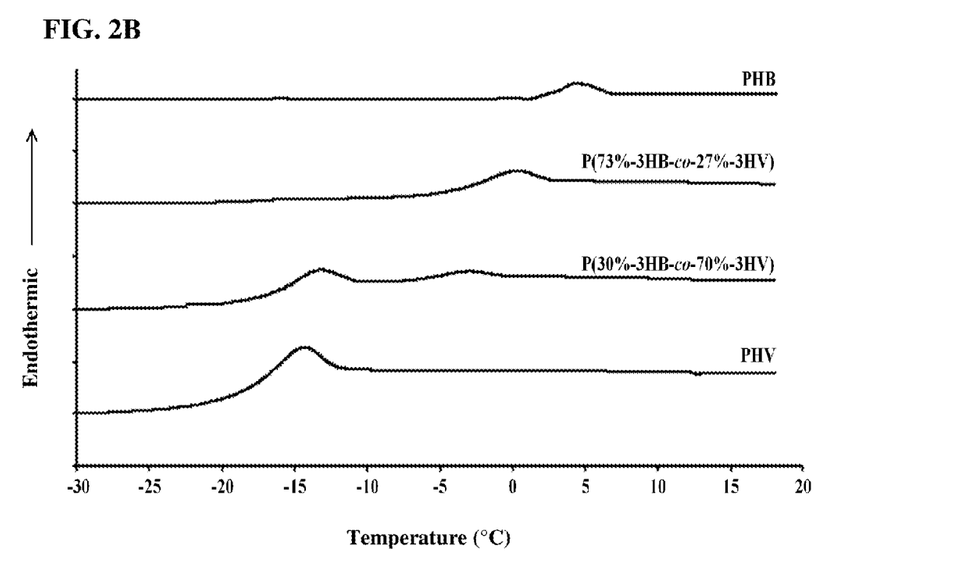

J/g), respectively (see FIG. 2A). In addition, it was shown that the $T_m$ did not vary as the polymers aged however; the enthalpy of fusion ($\Delta H_m$) did show slight increases over the aging process. These increases demonstrated that more energy was required to melt the crystalline portions of the polymers, which generally is indicative of the presence of a more crystalline structure. This may be at least part of the reason that the elongation at break and fracture energy reduced for each of the polymer films upon aging. Another interesting observation was that the PHB/V copolymer containing 70 mol % 3-HV showed 2 $T_g$'s (see FIG. 2B), one at −15° C., which is characteristic of polymers containing a high 3-HV content, and one at −5° C., which would seem to indicate the presence of higher 3-HB contents in at least a fraction of the PHB/V polymers produced from 0.5%:0.5% glycerol:levulinic acid. This phenomenon may be further proof of the preferential utilization of levulinic acid in the formation of 3-HV intermediates early in the fermentation leaving more glycerol for the synthesis of 3-HB intermediates for later polymerizations.

TABLE 5

Mechanical/tensile properties of the PHA polymers derived from 10-L bench-top batch fermentations in the presence of varying ratios of glycerol and levulinic acid (LA).

| Sample #[a] (Film age) | Tensile Strength[b] (MPa) | Elongation at Break[b] (%) | Fracture Energy[b] (J/cm³) | Modulus[b] (MPa) |
|---|---|---|---|---|
| 1; (3 days) | 19.1 ± 0.4 | 14.6 ± 4.9 | 2.1 ± 0.8 | 593.9 ± 30.6 |
| (2 mos.) | 23.5 ± 0.8 | 4.0 ± 0.2 | 0.4 ± 0.03 | 1532.3 ± 3.0 |
| 2; (3 days) | 13.6 ± 0.2 | 261.3 ± 73.8 | 31.4 ± 9.6 | 406.7 ± 16.7 |
| (2 mos.) | 17.6 ± 0.2 | 43.3 ± 2.6 | 5.8 ± 0.7 | 664.4 ± 57.9 |
| 3; (3 days) | 17.3 ± 1.4 | 609.3 ± 159.9 | 89.5 ± 27.4 | 228.8 ± 36.3 |
| (2 mos.) | 17.3 ± 0.7 | 32.1 ± 0.9 | 4.4 ± 0.04 | 518.0 ± 41.1 |
| 4; (3 days) | 15.6 ± 1.1 | 203.1 ± 87.2 | 31.2 ± 15.5 | 390.9 ± 11.1 |
| (2 mos.) | 17.9 ± 1.6 | 27.8 ± 1.9 | 4.2 ± 0.1 | 580.8 ± 10.0 |

[a]Samples 1-4 were produced from glycerol:levulinic acid ratios (in wt %) of 1.0:0, 0.75:0.25, 0.5:0.5 and 0.25:0.75, respectively.
[b]All tabulated values are based on averages of at least 3 measurements.

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention.

We claim:

1. A tunable method for producing at least one polyhydroxyalkanoate biopolymer comprising:
   a. providing a carbon source of glycerol, levulinic acid, and mixtures thereof in a tunable amount that drives the microbial synthesis of said at least one polyhydroxyalkanoate biopolymer in a fermentation medium,
   b. providing a microorganism in said same fermentation medium capable of synthesizing said at least one polyhydroxyalkanoate biopolymer using as a carbon source a tunable amount of glycerol, levulinic acid, and mixtures thereof that drives the microbial synthesis of said at least one polyhydroxyalkanoate biopolymer, and
   c. recovering said at least one polyhydroxyalkanoate biopolymer; wherein said at least one polyhydroxyalkanoate biopolymer is biocompatible and biodegradable polyester; and wherein said at least one polyhydroxyalkanoate biopolymer is selected from the group consisting of poly-3-hydroxybutyrate, poly-3-hydroxyvalerate, and poly-3-hydroxybutyrate-co-3-hydroxyvalerate; and wherein said tunable method further comprises varying said carbon source in said fermentation medium, wherein said microorganism is selected from the group consisting of *Pseudomonas* ssp., *Pseudomonas oleovorans*, *Ralstonia* spp., *Ralstonia eutropha* and mixtures thereof.

2. The method of claim 1 wherein said carbon source is a mixture of glycerol and levulinic acid.

3. The method of claim 2 wherein said mixture of glycerol and levulinic acid can be varied to control the monomer composition and mechanical properties of said at least one polyhydroxyalkanoate biopolymer.

4. The method of claim 1 wherein when a first ratio of glycerol to levulinic acid is approximately 1.0% to approximately 0% w/v, said polyhydroxyalkanoate biopolymer produced is approximately 100 mol % poly-3-hydroxybutyrate, when a second ratio of glycerol to levulinic acid is approximately 0.2% to approximately 0.8% w/v, said polyhydroxyalkanoate biopolymer produced is approximately 100 mol % poly-3-hydroxyvalerate, and when a third ratio of glycerol to levulinic acid is between said first ratio and said second ratio said polyhydroxyalkanoate biopolymer produced is poly-3-hydroxybutyrate-co-3-hydroxyvalerate with varying mol % of 3-hydroxybutyrate and 3-hydroxyvalerate.

5. The method of claim 1, wherein said tunable method further comprising varying the time of fermentation.

* * * * *